(12) United States Patent
Sharda et al.

(10) Patent No.: US 8,348,839 B2
(45) Date of Patent: Jan. 8, 2013

(54) SYSTEMS AND METHODS FOR ACTIVE LISTENING/OBSERVING AND EVENT DETECTION

(75) Inventors: Pallav Sharda, Palatine, IL (US); Steven Eric Linthicum, Lake in the Hills, IL (US)

(73) Assignee: General Electric Company, Schenectady, NY (US)

( * ) Notice: Subject to any disclaimer, the term of this patent is extended or adjusted under 35 U.S.C. 154(b) by 1271 days.

(21) Appl. No.: 11/733,545

(22) Filed: Apr. 10, 2007

(65) Prior Publication Data

US 2008/0255428 A1 Oct. 16, 2008

(51) Int. Cl.
*A61B 5/00* (2006.01)
*G10L 11/00* (2006.01)
(52) U.S. Cl. .............. 600/300; 600/301; 704/200
(58) Field of Classification Search ........... 704/200
See application file for complete search history.

(56) References Cited

U.S. PATENT DOCUMENTS

| | | | | |
|---|---|---|---|---|
| 4,933,873 A * | 6/1990 | Kaufman et al. | ............ | 704/270 |
| 5,448,680 A * | 9/1995 | Kang et al. | ............ | 704/225 |
| 5,683,423 A * | 11/1997 | Post | ............ | 607/5 |
| 6,406,426 B1 * | 6/2002 | Reuss et al. | ............ | 600/300 |
| 6,594,634 B1 * | 7/2003 | Hampton et al. | ............ | 705/3 |
| 6,766,328 B2 | 7/2004 | Stefanchik | | |
| 6,849,045 B2 | 2/2005 | Iliff | | |
| 6,997,873 B2 | 2/2006 | Bardy | | |
| 7,120,488 B2 * | 10/2006 | Nova et al. | ............ | 607/2 |
| 7,426,468 B2 * | 9/2008 | Coifman et al. | ............ | 704/275 |
| 7,436,311 B2 * | 10/2008 | Rapaport et al. | ............ | 340/573.1 |
| 7,627,470 B2 * | 12/2009 | Manabe et al. | ............ | 704/231 |
| 7,752,050 B1 * | 7/2010 | Hameed et al. | ............ | 704/275 |
| 7,925,508 B1 * | 4/2011 | Michaelis | ............ | 704/270 |
| 2003/0101078 A1 * | 5/2003 | Voegeli et al. | ............ | 705/2 |
| 2003/0195775 A1 * | 10/2003 | Hampton et al. | ............ | 705/3 |
| 2004/0064342 A1 * | 4/2004 | Browne et al. | ............ | 705/2 |

(Continued)

FOREIGN PATENT DOCUMENTS

EP 1262142 A2 4/2002

(Continued)

OTHER PUBLICATIONS

GB Intellectual Property Office, Examination Report Under Section 18(3), Application No. GB0806201.0; Jul. 4, 2011; 2 pages.

*Primary Examiner* — Sam Yao
*Assistant Examiner* — Bobby Soriano

(57) ABSTRACT

Embodiments of the present invention provide a method of monitoring an environment comprising: monitoring at least one data stream wherein the data stream is a data stream in the environment; detecting a specified event from the data stream; and triggering a response to the specified event. Embodiments of the present invention provide a system for monitoring an environment comprising: a receiver adapted to receive at least one input data stream wherein the input data stream is a data stream in the environment; an active listener/observer system adapted to monitor the data stream; and an interface adapted to express at least one output stream. Embodiments of the present invention provide a computer-readable medium having instructions comprising: an active listener/observer routine configured to monitor at least one data stream; a detection routine configured to find specified events in the data stream; and an output routine configured to express a response event.

18 Claims, 3 Drawing Sheets

U.S. PATENT DOCUMENTS

| | | | |
|---|---|---|---|
| 2004/0127241 A1* | 7/2004 | Shostak | 455/500 |
| 2004/0172069 A1* | 9/2004 | Hakala | 607/5 |
| 2004/0172070 A1* | 9/2004 | Moore et al. | 607/5 |
| 2004/0249778 A1* | 12/2004 | Iliff | 706/45 |
| 2004/0254791 A1* | 12/2004 | Coifman et al. | 704/246 |
| 2005/0146431 A1* | 7/2005 | Hastings et al. | 340/539.12 |
| 2005/0148890 A1* | 7/2005 | Hastings | 600/509 |
| 2005/0165285 A1* | 7/2005 | Iliff | 600/300 |
| 2006/0053002 A1* | 3/2006 | Visser et al. | 704/200 |
| 2006/0058591 A1* | 3/2006 | Garboski et al. | 600/301 |
| 2006/0143043 A1* | 6/2006 | McCallie et al. | 705/2 |
| 2006/0161457 A1* | 7/2006 | Rapaport et al. | 705/2 |
| 2007/0057798 A1* | 3/2007 | Li et al. | 340/573.1 |
| 2007/0185736 A1* | 8/2007 | Cervi et al. | 705/2 |
| 2007/0208263 A1* | 9/2007 | John et al. | 600/509 |
| 2007/0250191 A1* | 10/2007 | Rourke et al. | 700/90 |
| 2008/0081956 A1* | 4/2008 | Shah et al. | 600/300 |
| 2008/0181417 A1* | 7/2008 | Pereg et al. | 381/17 |

FOREIGN PATENT DOCUMENTS

| | | |
|---|---|---|
| GB | 2217953 A | 7/2008 |
| WO | 2007150004 A2 | 12/2007 |

* cited by examiner

SYSTEMS AND METHODS FOR ACTIVE LISTENING/OBSERVING AND EVENT DETECTION

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Generally, the technical field involves information systems for active listening/observing and event detection. Specifically, it involves an active listener/observer healthcare information system for event detection.

The amount of information flowing through a high-activity environment, such as a healthcare delivery environment, can be immense. As technology progresses and more information becomes available, a user cannot be expected to keep track of all of the information and maintain a high-level picture of the situation. This problem can be exacerbated where the immense information comes from disparate, loosely integrated information technology systems.

In a hospital emergency department or intensive care unit, for example, there are a number of sources of important information. These sources can include caregiver conversations, comments made by the patient, monitoring devices, lab information systems, intensive care unit information systems and other hospital information systems. It is extremely difficult for an individual caregiver to keep track of all this disparate information and maintain a high-level picture of the patient's needs. This is particularly important where the information may deal with a matter of life and death.

Early identification of problems and response to those problems can have significant impact on the user's ability to remedy the problems. For example, earlier identification of critically ill patients or emergent situations could allow for earlier intervention which could significantly impact survival. Earlier detection of a "Code Blue" callout by a caregiver (a term used by caregiver's to represent a real or suspected imminent loss of life) or critical patient vitals on a physiological monitoring device could allow for earlier response which could potentially save a patient's life.

There is a surfacing clinical problem with identifying critically ill patients at an earlier stage when intervention can have significant impact on survival. Hospitals have responded to this problem by creating rapid response teams, or RRT's, typically consisting of an MD, an RN and a respiratory therapist. These teams are available 24 hours per day to respond quickly and stabilize the patient in an emergency situation. In the past four years the number of RRT's nationwide has skyrocketed. However, no significant improvements have been made to tackle the same problem through use of healthcare information systems.

Current information systems seek a particular data stream, or data input, from the user, detect important elements of the provided data stream and give a desired response. However, these systems do not actively monitor an environment for potential problems. The monitoring aspect of current systems depends on explicit data input from the user (or other networked system) as a trigger. These systems provide a response only when potentially problematic data is detected in this manner. Today's systems do not actively monitor background activity in a high-activity environment and respond to problematic data.

Accordingly, it would be desirable to develop an information system for event detection that does not depend on direct input from a user. In the healthcare field, it would be desirable to develop an active listener/observer information system that monitors background data streams and triggers response events.

BRIEF SUMMARY OF THE INVENTION

Certain embodiments of the present invention provide systems and methods for active listening/observing and event detection.

Certain embodiments provide methods of monitoring an environment comprising: monitoring at least one data stream wherein the data stream is a data stream in the environment; detecting a specified event from the data stream; and triggering a response to the specified event. These steps can be performed sequentially or in another order. In some embodiments of the method multiple data streams are monitored.

The monitored data stream may be a conversation or statement. In an embodiment, speech recognition equipment may be used. In another embodiment, the speech recognition equipment differentiates between speakers.

In yet another embodiment the data stream is inputted through an electronic data interchange.

Some embodiments monitor the data stream or data streams using an active listener/observer. The active listener/observer may be used to monitor background data streams.

In some embodiments the response is an alert. In other embodiments the response is an automated event log. In yet other embodiments the response is an enterprise event. Multiple responses may be triggered by one event.

The monitored environment may be a healthcare environment. In the healthcare environment the data stream may be a caregiver conversation or statement, a physiological monitoring device, or data from a healthcare information technology system.

Certain embodiments provide a system for monitoring an environment comprising: a receiver adapted to receive at least one input data stream wherein the input data stream is a data stream in the environment; an active listener/observer system adapted to monitor the data stream; and an interface adapted to express at least one output stream.

In one embodiment of the system for monitoring an environment the active listener/observer system and the interface are combined.

Certain embodiments provide a computer-readable medium having a set of instructions for execution by a computer, the set of instructions comprising: an active listener/observer routine configured to monitor at least one data stream; a detection routine configured to find specified events in the data stream; and an output routine configured to express a response event.

These and other features of the present invention are discussed or apparent in the following detailed description.

Figure 1:
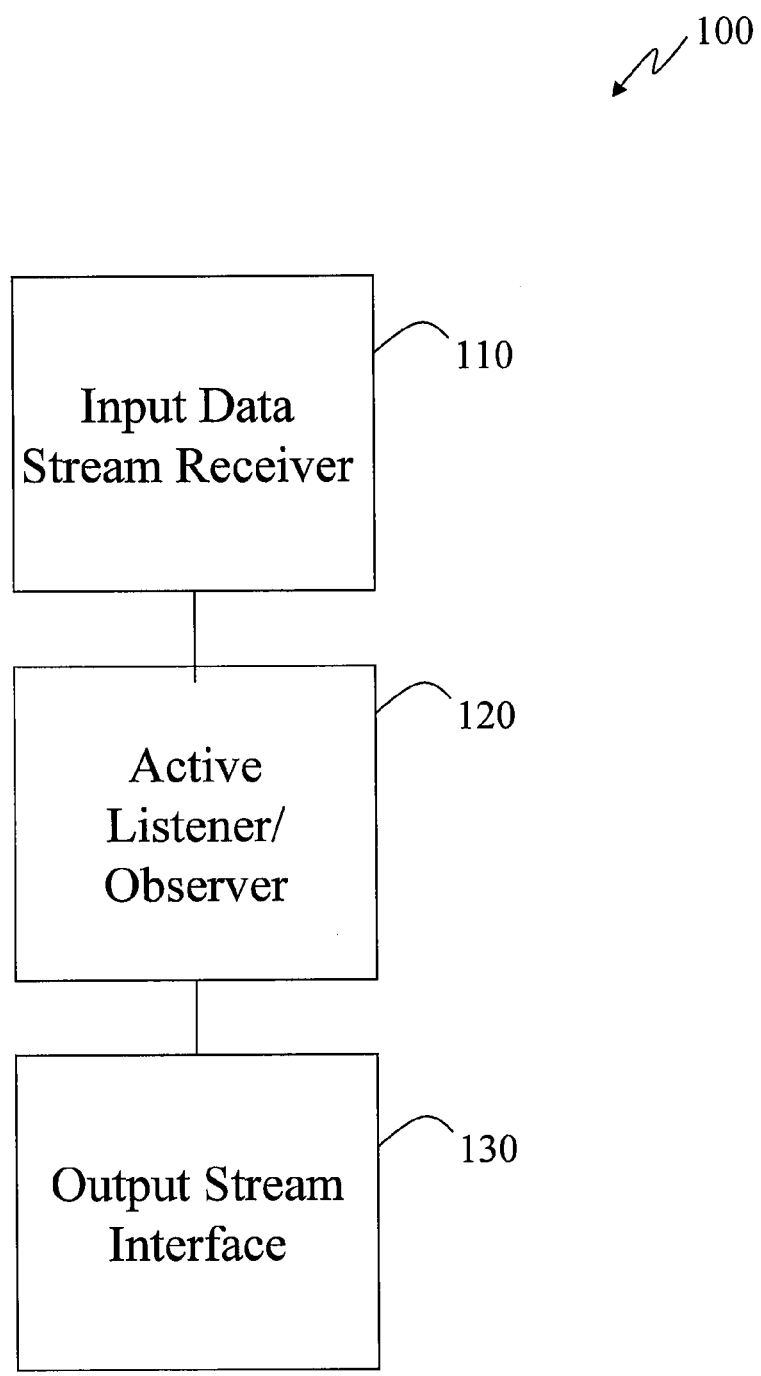
FIG. 1 illustrates a high-level schematic of a system for active listening/observing and event detection according to an embodiment the present disclosure.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

The current disclosure relates to an information system and method for active listening/observing and event detection. Although a healthcare information system is used as an example, the current disclosure should not be viewed as limited to healthcare related information systems.

Due to the immense amount of information flowing through a high-activity environment, a single user cannot be expected to keep track of all of the information and maintain a high-level picture of the situation. This problem can be exacerbated where the immense information comes from disparate, loosely integrated information technology systems. Early identification of problems and response to those problems can have significant impact on the user's ability to remedy the problems.

Information systems can be used to monitor and respond to problems in a high-activity environment. FIG. 1 illustrates a system (100) for event detection according to an embodiment of the present disclosure. The information system (100) is made up of a receiver (110) for either a single input data stream or multiple input data streams. The information system (100) has an active listener/observer (120) that is used to monitor for a certain event or multiple events. When an event is detected, the information system (100) can trigger an output stream or multiple output streams using an interface (130) as a response event. The receiver (110) communicates with the active listener/observer (120). The active listener observer communicates with the output stream interface (130).

The components of the system (100) may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain components may be integrated in various forms and/or may be provided as software and/or interface to other systems/software and/or other functionality on a computing device, such as a computer. Certain embodiments may omit one or more of the components of the system (100).

Possible input data streams include conversations or comments made by an individual in the environment. Speech recognition software, programs and/or devices (speech recognition equipment) can be used. Another possible data input stream includes data inputted into an electronic data interchange or interface with other information system(s). This would involve a user inputting data into an information system, possibly using an input device, such as a keyboard, a touchscreen, a joystick, a mouse, a touchpad, and/or a microphone could also be used. Yet another possible data input stream would be monitors and gauges that measure a variable, such as temperature or pressure. A single data input stream or multiple data input streams could exist.

The active listener/observer (120) monitors the various data input streams. The active listener/observer (120) is programmed to detect specified events using keyword knowledge and context information. The active listener/observer (120) has the ability to monitor multiple data streams, including background data. The active listener/observer (120) can also analyze the multiple data streams in context with each other. This allows the active listener/observer (120) to monitor the overall situation not just one aspect. For example, a combination of data from separate data streams might indicate a problematic situation. In this case, the active listener/observer (120) would have the benefit of viewing the data streams in conjunction with each other.

Output streams could include alerts. Possible alerts include the triggering of an alarm, contacting a certain individual (charge nurse, attending physician, EKG technician, etc.) or contacting an emergency agency, such as the fire department, police department or a certain hospital team, such as a Rapid Response Team. Alternatively the output stream could be an automated event log. The automatic log would keep a record or transcript of how a certain problem was addressed. This report could prove useful for quality control reports or if there is litigation regarding the problem. The output stream could alternatively be the triggering of an enterprise event such as automatically locking doors, engaging a sprinkler system or automated system events in one or more information systems, such as a page to an attending physician or operating room nurse for example. One event could trigger one or multiple outputs streams.

One example of a high-activity environment is a healthcare environment, such as a hospital emergency department or intensive care unit. In these healthcare environments there are a number of sources of important information. It is extremely difficult for an individual caregiver to keep track of all this disparate information and maintain a high-level picture of the patient's needs. There is a surfacing clinical problem with identifying critically ill patients and urgent situations at an earlier stage when intervention can have significant impact on survival.

Figure 2:
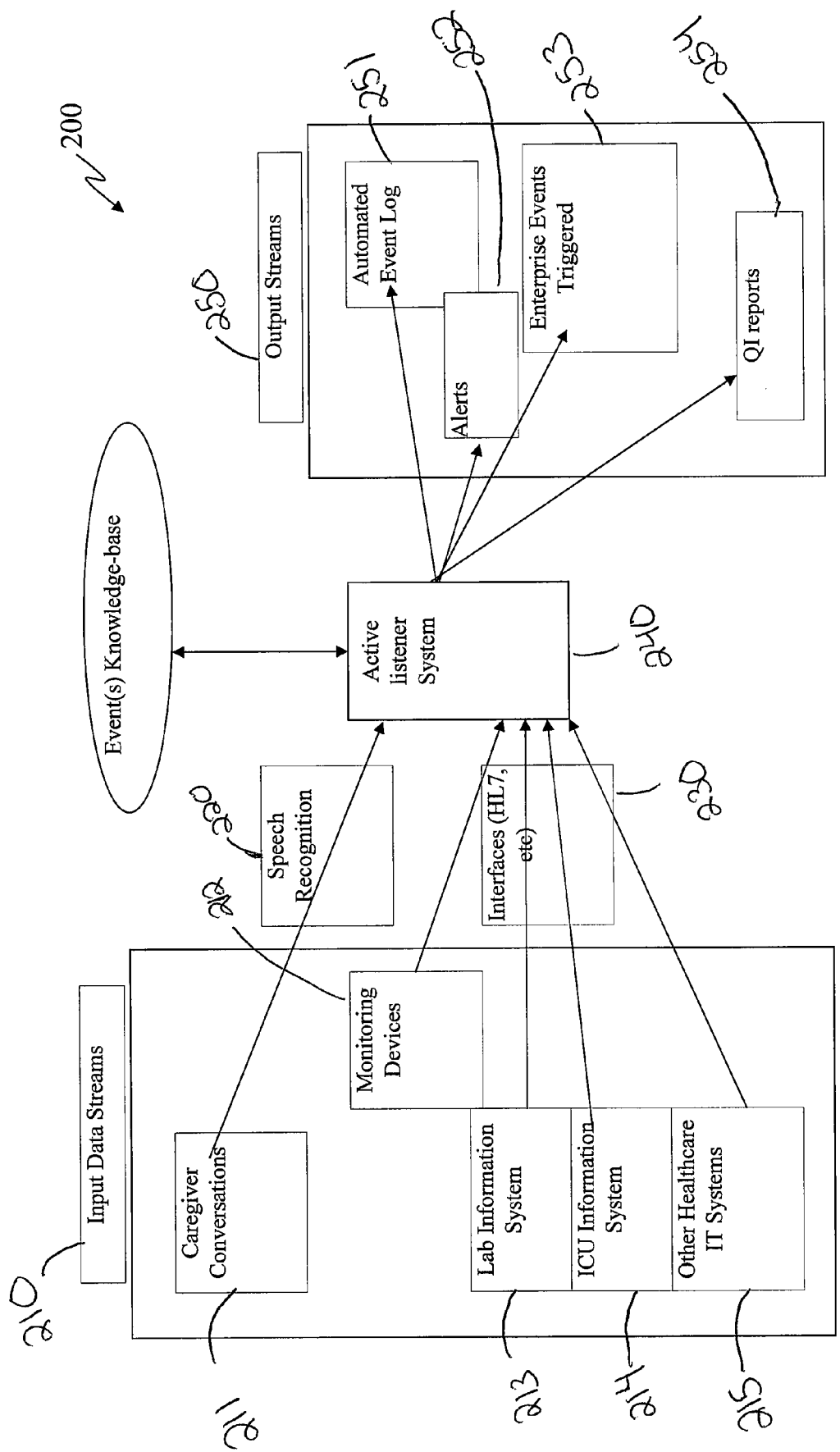
FIG. 2 illustrates a healthcare information system for active listening/observing and event detection according to an embodiment the present disclosure.

A specialized healthcare information system can be used to monitor and respond to problems in a high-activity environment. FIG. 2 illustrates a healthcare information system (200) for event detection according to an embodiment of the present invention. In a high-activity healthcare environment, an information system can monitor multiple input data streams (210). Possible data streams include caregiver conversations (211), statements made by the patient, data from lab information systems (213), data from intensive care unit information systems (214), data from other hospital information systems (215), and information from monitoring devices (212).

The components of the system (200) may be implemented alone or in combination in hardware, firmware, and/or as a set of instructions, or rules, in software, for example. Certain embodiments may be provided as a set of instructions residing on a computer-readable medium, such as a memory, hard disk, DVD, or CD, for execution on a general purpose computer or other processing device. Certain components may be integrated in various forms and/or may be provided as software and/or other functionality on a computing device, such as a computer. Certain embodiments may omit one or more of the components of the system (200).

Caregiver conversation can be monitored using speech recognition software, programs and/or devices (speech recognition equipment) (220). The speech recognition equipment (220) would allow the active listener/observer (240) to pick up and monitor vocal cues. In one embodiment, the speech recognition software, program and/or device (220) could differentiate between speakers. This would allow the active listener/observer (240) to differentiate between comments made by a patient, nurse or doctor and respond accordingly.

The data from various healthcare information systems (215) can be inputted by a user possibly through a keyboard or similar device. This could also be done using an electronic data interchange interface (230). One specific example is a Health Level 7 healthcare data interchange format (230) that facilitates such data interfaces.

The information system (200) has an active listener (240) that monitors and detects specified events. The active listener/observer (240) can detect specified events using keyword knowledge and context information. For example, the active listener/observer (240) could detect a "Code Blue" callout by a caregiver (a term used by caregiver's to represent a real or suspected imminent loss of life) or critical patient vitals on a monitoring device.

As discussed above, the active listener/observer (240) can also analyze the multiple data streams in context with each other. This allows the active listener/observer to monitor the patient's overall situation. For example, a combination of data from the caregiver's comments and the data from physiological monitors could indicate a dangerous situation. The active listener/observer (240) would have the benefit of viewing the data streams in conjunction with each other, which could help to identify the problem earlier and more precisely.

When problematic events are detected the system can trigger an output stream (250) or multiple output streams (250). Possible output streams include an enterprise information system event (253), an alert (such as a hardware alert to a pager or a software message pop-up for example) (252), an automated event log or transcript (251), or a quality indicator report (254). For example, the system could page an attending doctor or the Rapid Response Team. The system could also maintain a log of resuscitation activities with timestamps and voice identifications. This type of event log or transcript could be the basis of care quality related research for hospitals by allowing them to study the time delay between a code callout and the first assistance. Log information can also be helpful when the hospital or caregiver faces a legal challenge regarding the care provided.

Figure 3:
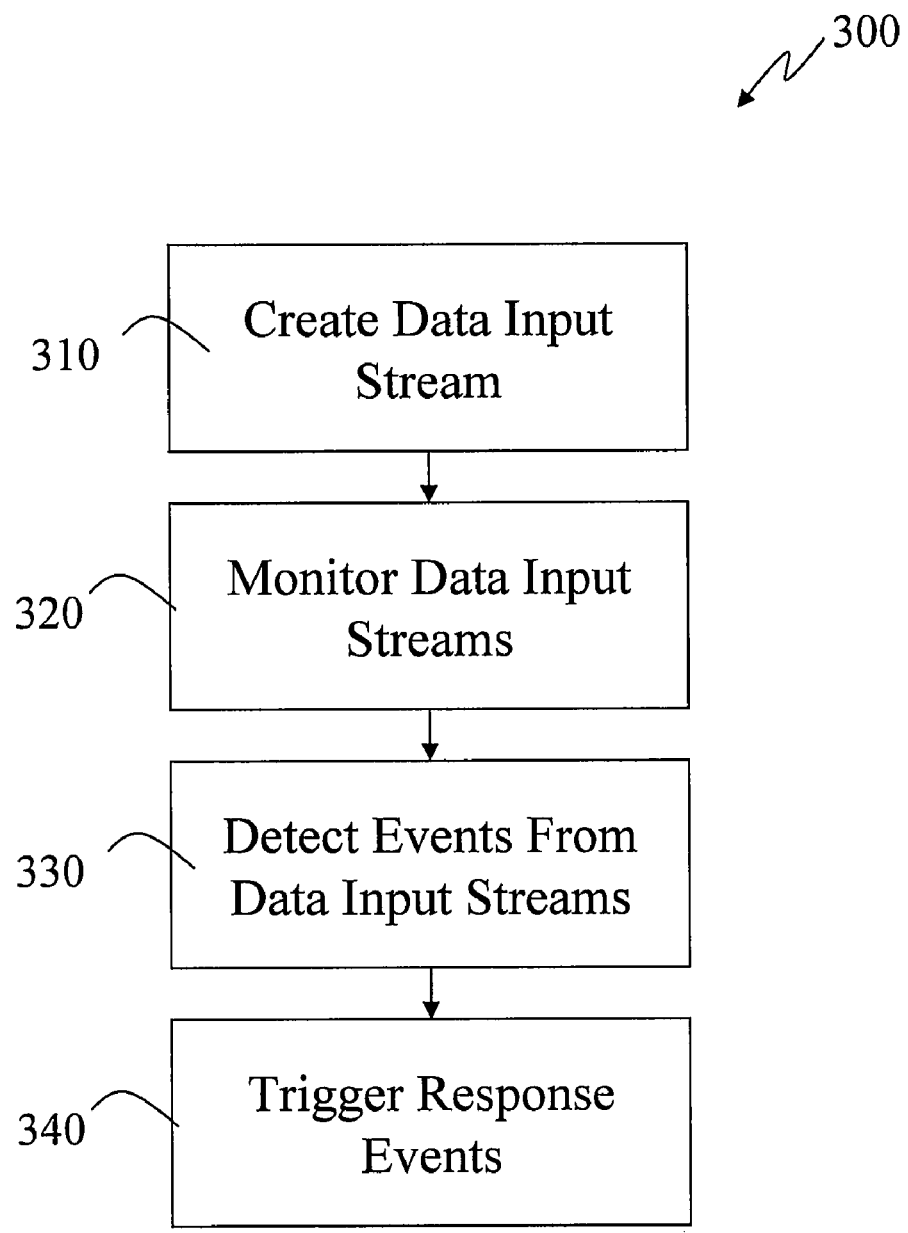
FIG. 3 illustrates a flow diagram for active listening/observing and event detection according to an embodiment the present disclosure.

FIG. 3 illustrates a method of monitoring data streams and triggering response events (300). The method includes creating a data input stream (310), monitoring data input streams (320), detecting certain events from those data input streams (330) and triggering response events when the certain events are detected (340).

One or more of the steps of the method (300) may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments may be implemented in one or more of the systems described above. For example, certain embodiments of the method (300) may be implemented using one or more local EMR systems, a database or other data storage storing electronic data, and one or more user interfaces facilitating monitoring data streams and triggering response events.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

An input data stream receiver may receive data input streams. The input data stream receiver may be similar to (110) as described above, for example. The data input streams could be conversations or statements made by individuals in the environment. These vocal streams could be monitored with the assistance of speech recognition software, programs and/or devices. In one scenario the speech, recognition software, program and/or device could differentiate between speakers.

Another possible data input stream includes data inputted by a user. This could utilize an electronic data interchange, such as the Health Level 7 interchange commonly used in the health industry. An input device such as a keyboard, a touchscreen, a joystick, a mouse, a touchpad, and/or a microphone could also be used.

Yet another possible data input stream could come from gauges or monitors within the environment. The monitors or gauges would measure certain variables, including electrophysiological parameters in a healthcare setting. Possible examples include pressure, temperature, depth, altitude, blood pressure, heart rate, etc.

The data input streams are monitored (320) in order to detect specified events (330). Monitoring is done by actively listening and/or observing data streams in an environment. Detection is done by using keyword knowledge and context information. An active listener/observer can be used for both purposes. The active listener/observer may be similar to (120) or (240) described above, for example. The active listener/observer listens to and observes data streams in a given environment. The active listener/observer is programmed to watch for certain keywords or pieces of data that may indicate a specified event.

One or more data streams may be monitored at any given time. Monitoring of multiple data streams allows the data from one stream to be analyzed in conjunction with the data from other streams. This allows for better detection of problems. This is particularly helpful where one data stream does not indicate a problem by itself but may indicate a problem when viewed in light of information in other data streams.

Once a specified event is detected a response event is triggered (340). The response event can be expressed through an output stream interface. The output stream interface may be similar to (130) or (250) described above, for example. A possible response event is an alert, such as the triggering of an alarm, contacting a certain individual or contacting an emergency agency. The response event could also be an automated event log. The automatic log would keep a record of how a certain problem was addressed. This report could prove useful for quality control reports or if there is later litigation regarding an event. In yet another embodiment, a response event could include specific response actions, such as the locking or unlocking of doors, the activation of a sprinkler system, etc. One ore more response events may be triggered.

For example, a caregiver creates input data streams as he or she talks during patient care. Speech recognition equipment identifies the voice as that of the caregiver and converts the vocal statement into a computer readable form. An active listener/observer can monitor the caregiver's comments. If a patient's vitals start slipping and create a life-threatening situation, the caregiver would make a "Code Blue" callout. The active listener/observer identifies a "Code Blue" callout by a caregiver as a specified event to which a response is necessary. In response the rapid response team is automatically paged to begin resuscitation activities. The response activity or pattern logic can be coded and stored in the active listener/observer system itself, or it could reside in an external system/application that interfaces with the listener/observer system.

In another example, the patient is attached to monitoring devices which create data input streams regarding the patient's vital signs. The active listener/observer once again monitors the data input streams from the monitoring devices. If the patient's vitals start to drop and create a life-threatening situation, the data streams from the monitoring devices would indicate this problem. The active listener/observer would identify the dropping vital signs as a specified event to which a response is necessary. In response an automated event log is started to keep track of resuscitation activities for litigation or quality control.

Thus, certain embodiments provide the benefit of background event detection. Certain embodiments also provide the benefit of monitoring data streams and triggering response events. Particularly, certain embodiments actively listen and observe the many date streams in an environment and trigger response events. Thus allowing for earlier detection and response to problems.

While particular elements, embodiments and applications of the present invention have been shown and described, it will be understood, of course, that the invention is not limited thereto since modifications can be made by those skilled in the art without departing from the scope of the present disclosure, particularly in light of the foregoing teachings.

The invention claimed is:

1. A method of monitoring a healthcare environment for purposes of early event detection comprising:
   actively monitoring a healthcare environment for speech input using a microphone to input speech from the healthcare environment;
   activating a speech recognition program in real time upon detection of the speech input to interpret the speech;
   using a computer processor to compare the interpreted speech to keywords in a database; and
   if the interpreted speech matches a keyword in the database, triggering a response event for the actively monitored healthcare environment that includes outputting an alert and activating an event log that includes a listing of at least one of resuscitation activities and voice identifications,
   wherein the speech input at the microphone is actively monitored in substantially real-time using the speech recognition program to interpret the speech and the computer processor to compare the interpreted speech to keywords in the database.

2. The method of claim 1 wherein the steps are performed sequentially.

3. The method of claim 1 wherein the alert includes at least one of contacting an individual, contacting an agency, initiating a page and initiating a software message pop-up.

4. The method of claim 1 further comprising:
   differentiating between speech of a plurality of speakers in the healthcare environment.

5. The method of claim 1 further comprising:
   using an input device to input data, wherein the input device includes at least one of a keyboard, a touchscreen, a joystick, a mouse and a touchpad; and
   outputting an alert based on the input data.

6. The method of claim 1 further comprising:
   triggering an enterprise event if the interpreted speech matches a keyword in the database, wherein the enterprise event includes at least one of locking a door and activating a sprinkler system.

7. The method of claim 1 wherein multiple alerts are triggered.

8. The method of claim 1 further comprising:
   using a physiological monitoring device to input patient data; and
   outputting an alert based on the patient data.

9. The method of claim 1 further comprising:
   inputting information from a healthcare information system; and
   outputting an alert based on the information from the healthcare information system.

10. A healthcare environment monitoring system comprising:
    a microphone configured to input speech from a healthcare environment in order to actively monitor the healthcare environment, wherein the speech is interpreted in real time upon detection of the speech input using a speech recognition program; and
    a computer processor configured to compare the interpreted speech to keywords in a database, the processor configured such that if the interpreted speech matches a keyword in the database, the processor triggers a response event for the actively monitored healthcare environment, the response event including outputting an alert and activating an event log that includes a listing of at least one of resuscitation activities and voice identifications,
    wherein the speech input at the microphone is actively monitored in substantially-real time by the speech recognition program and the computer processor.

11. The system of claim 10, wherein the alert includes at least one of contacting an individual, contacting an agency, initiating a page and initiating a software message pop-up.

12. The system of claim 10 wherein the speech recognition program is configured to differentiate between a plurality of speakers in the healthcare environment.

13. The system of claim 10 further comprising:
    an input device configured to input data, wherein the input device includes at least one of a keyboard, a touchscreen, a joystick, a mouse and a touchpad, and wherein the processor is configured to initiate an alert based on the input data.

14. The system of claim 10 wherein the processor is configured to initiate an enterprise event if the interpreted speech matches a keyword in the database, and wherein the enterprise event includes at least one of locking a door and activating a sprinkler system.

15. The system of claim 10 wherein the processor is configured to initiate multiple alerts.

16. The system of claim 10 further comprising:
    a physiological monitoring device configured to input patient data, and wherein the processor is configured to initiate an alert based on the patient data.

17. The system of claim 10 further comprising:
    an input receiver configured to input information from a healthcare information system, and wherein the processor is configured to initiate an alert based on the information from the healthcare information system.

18. A non-transitory computer-readable medium having a set of instructions for execution by a computer, the set of instructions comprising:
    a first routine configured to allow speech to be interpreted that is input from a microphone actively monitoring a healthcare environment for the speech input; and
    a second routine configured to compare the interpreted speech to keywords in a database, the second routine configured such that if the interpreted speech matches a keyword in the database, the second routine triggers a response event for the actively monitored healthcare environment, the response event including outputting an alert and activating an event log that includes a listing of at least one of resuscitation activities and voice identifications, wherein the input from the microphone is actively monitored in substantially real-time upon detection of the speech input to interpret the speech using the second routine.

* * * * *